(12) United States Patent
Sharma et al.

(10) Patent No.: US 10,478,130 B2
(45) Date of Patent: Nov. 19, 2019

(54) PLAQUE VULNERABILITY ASSESSMENT IN MEDICAL IMAGING

(71) Applicant: SIEMENS HEALTHCARE GMBH, Erlangen (DE)

(72) Inventors: Puneet Sharma, Monmouth Junction, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 758 days.

(21) Appl. No.: 14/973,390

(22) Filed: Dec. 17, 2015

(65) Prior Publication Data

US 2016/0235373 A1 Aug. 18, 2016

Related U.S. Application Data

(60) Provisional application No. 62/115,713, filed on Feb. 13, 2015.

(51) Int. Cl.
*A61B 5/00* (2006.01)
*A61B 5/02* (2006.01)
(Continued)

(52) U.S. Cl.
CPC ............ *A61B 5/7275* (2013.01); *A61B 5/021* (2013.01); *A61B 5/026* (2013.01);
(Continued)

(58) Field of Classification Search
CPC ........... A61B 5/7275; A61B 8/06; A61B 8/12; A61B 8/085; A61B 5/7267; A61B 5/021; A61B 6/461; A61B 5/14546; A61B 8/5223; A61B 6/5217; A61B 8/0891; A61B 6/504; A61B 5/055; A61B 5/02007; A61B 5/026; A61B 5/742; G16H 10/40; G16H 50/50; G16H 50/30; G16H 30/40

See application file for complete search history.

(56) References Cited

U.S. PATENT DOCUMENTS 8,526,699 B2 9/2013 Mittal et al.
8,582,854 B2 11/2013 Zhang et al.
(Continued)

FOREIGN PATENT DOCUMENTS

CN 101799864 A 8/2010
CN 0N102194049 A 9/2011
(Continued)

OTHER PUBLICATIONS

Achenbach, Stephan, and Paolo Raggi. "Imaging of coronary atherosclerosis by computed tomography." European heart journal (2010).

(Continued)

*Primary Examiner* — Sanjay Cattungal

(57) ABSTRACT

Rather than rely on variation from physician to physician and limited imaging information for assessing plaque vulnerability of a patient, medical imaging and other information are used by a machine-implemented classifier to predict plaque rupture. Anatomical, morphological, hemodynamic, and biochemical features are used in combination to classify plaque.

15 Claims, 2 Drawing Sheets

(51) Int. Cl.
- A61B 5/055 (2006.01)
- A61B 6/00 (2006.01)
- A61B 8/08 (2006.01)
- A61B 5/145 (2006.01)
- A61B 5/021 (2006.01)
- A61B 5/026 (2006.01)
- A61B 6/03 (2006.01)

(52) U.S. Cl.
CPC .......... *A61B 5/02007* (2013.01); *A61B 5/055* (2013.01); *A61B 5/14546* (2013.01); *A61B 5/7267* (2013.01); *A61B 6/461* (2013.01); *A61B 6/504* (2013.01); *A61B 6/5217* (2013.01); *A61B 8/0891* (2013.01); *A61B 8/5223* (2013.01); *A61B 5/742* (2013.01); *A61B 6/032* (2013.01)

(56) References Cited

U.S. PATENT DOCUMENTS

| | | | |
|---|---|---|---|
| 8,744,151 | B2 | 6/2014 | Hirano et al. |
| 9,125,622 | B2 | 9/2015 | Kitamura |
| 9,129,417 | B2 | 9/2015 | Zheng et al. |
| 9,220,419 | B2 † | 12/2015 | Choi |
| 9,770,303 | B2 | 9/2017 | Choi et al. |
| 9,861,284 | B2 | 1/2018 | Taylor |
| 2007/0232883 | A1 | 10/2007 | Ilegbusi |
| 2009/0119337 | A1* | 5/2009 | Biedermann ....... G06F 19/3481 |
| 2010/0067760 | A1 | 3/2010 | Zhang et al. |
| 2010/0323377 | A1* | 12/2010 | Karsdal ................ C07K 14/775 435/7.93 |
| 2011/0224542 | A1 | 9/2011 | Mittal et al. |
| 2012/0065514 | A1* | 3/2012 | Naghavi ................ G16H 50/20 600/454 |
| 2013/0132054 | A1 | 5/2013 | Sharma et al. |
| 2013/0216110 | A1 | 8/2013 | Zheng et al. |
| 2013/0246034 | A1 | 9/2013 | Sharma et al. |
| 2014/0058715 | A1 | 2/2014 | Sharma et al. |
| 2017/0340393 | A1* | 11/2017 | Choi ................. A61B 5/02007 |
| 2018/0310888 | A1* | 11/2018 | Itu ........................ A61B 5/7264 |

FOREIGN PATENT DOCUMENTS

| | | |
|---|---|---|
| CN | 102548481 A | 7/2012 |
| CN | 103270513 A | 8/2013 |
| CN | 106061387 A | 10/2016 |
| WO | WO2010099016 A1 | 9/2010 |

OTHER PUBLICATIONS

Katus, et al. "Assessment of atherosclerotic plaque composition using 256 slice CT and association with biochemical markers." http:www.medical.philips.com/fi_fi/about/news/publications/medicamundi/korosoglouivanc-mueller-katus.wpd. Jul. 26, 2014.

Kim, Jongyoun, et al. "The role of critical shear stress on acute coronary syndrome." Clinical hemorheology and microcirculation 55.1 (2012): 101-109.

Korosoglou, et al. "Comprehensive bio-imaging using quantitative coronary plaque composition assessment and the high sensitive troponin T for the prediction of cardiac outcomes." Jan. 7, 2014 http://clinicaltrials.gov/show/NCT02030704.

Maehara, Akiko, et al. "Morphologic and angiographic features of coronary plaque rupture detected by intravascular ultrasound." Journal of the American College of Cardiology 40.5. p. 904-910. Sep. 4, 2002.

Norja, Silja, et al. "C-reactive protein in vulnerable coronary plaques." Journal of clinical pathology 60.5 (2007): 545-548.

Rubin, Jonathan, et al. "Association between high-sensitivity C-reactive protein and coronary plaque subtypes assessed by 64-slice coronary computed tomography angiography in an asymptomatic population." Circulation: Cardiovascular Imaging 4.3 (2011): 201-209.

Slager, C. J., et al. "The role of shear stress in the generation of rupture-prone vulnerable plaques." Nature Clinical Practice Cardiovascular Medicine 2.8 (2005): 401-407.

Stone, Peter H., et al. "Prediction of sites of coronary atherosclerosis progression: in vivo profiling of endothelial shear stress, lumen, and outer vessel wall characteristics to predict vascular behavior." Current opinion in cardiology 18.6 (2003): 458-470.

Yang, Dong Hyun, et al. "Association between C-reactive protein and type of coronary arterial plaque in asymptomatic patients: assessment with coronary CT angiography." Radiology 272.3 (2014): 665-673.

Office Action dated Dec. 10, 2018 in corresponding Chinese Patent Application No. 201610086127.9.

\* cited by examiner
† cited by third party

PLAQUE VULNERABILITY ASSESSMENT IN MEDICAL IMAGING

RELATED APPLICATIONS

The present patent document claims the benefit of the filing dates under 35 U.S.C. § 119(e) of Provisional U.S. patent application Ser. No. 62/115,713, filed Feb. 13, 2015, which is hereby incorporated by reference.

BACKGROUND

The present embodiments relate to plaque vulnerability assessment. One of the main goals for plaque analysis is to identify and characterize the vulnerability of a particular plaque to rupture. For plaques in critical vessels, such as the coronaries and cerebral arteries, the event of plaque rupture could be life threatening, leading to a heart attack (myocardial infarction) or stroke.

Multiple medical imaging modalities, such as computed tomography (CT), x-ray angiography (XA), optical coherence tomography (OCT), ultrasound (US), intra-vascular ultrasound (IVUS), and near-infra red spectroscopy (NIRS), have been used to analyze plaque in blood vessels. However, the ability to accurately predict plaque rupture may vary. Human prediction from the medical imaging may be subjective or vary depending on the person predicting.

BRIEF SUMMARY

By way of introduction, the preferred embodiments described below include methods, systems, instructions, and non-transitory computer readable media for assessing plaque vulnerability of a patient in medical imaging. Rather than rely on variation from physician to physician and limited imaging information, medical imaging and other information are used by a machine-implemented classifier to predict plaque rupture. Two or more of anatomical, morphological, hemodynamic, and biochemical features are used in combination to classify plaque.

In a first aspect, a method is provided for assessing plaque vulnerability of a patient in medical imaging. An anatomical feature of a vessel or plaque and a morphological feature of the plaque are extracted from a scan of the patient by a medical imaging scanner. A hemodynamic feature of the patient is obtained from a hemodynamic sensor or personalized model of the vessel based on the scan. A biochemical feature from a blood test of the patient is received at an interface. A machine-implemented classifier calculates a risk score for plaque rupture for the patient from the anatomical, morphological, hemodynamic, and biochemical features. The risk score for the patient is transmitted to a display.

In a second aspect, a system is provided for assessing plaque vulnerability of a patient in medical imaging. A medical scanner is configured to scan a vessel and plaque of a patient. A memory is configured to store one or more first features from a blood test. An image processor is configured to extract one or more second features of the vessel, plaque, or vessel and plaque from data of the scan and to determine a risk of rupture of the plaque from the first features, the second features, and a third feature for hemodynamics. An output is configured to output the risk of rupture of the plaque for the patient.

In a third aspect, a method is provided for assessing plaque vulnerability of a patient in medical imaging. A morphological characteristic of plaque of a patient, a hemodynamic characteristic, an anatomy characteristic of a vessel with the plaque, and a biochemical characteristic of the plaque are loaded as an input feature vector. The plaque of the patient is classified by a machine-trained classifier in response to the input feature vector. A result of the classifying is signaled to a user.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Although there is no mechanistic model that fully explains the formation, growth, and eventual rupture of plaque in arteries, there has been considerable research to identify the various physiological mechanisms of plaque rupture. Several factors have been linked to the propensity of a plaque to rupture, ranging from morphological characteristics of the plaque, hemodynamic characteristics (e.g., wall shear stress), anatomy of the parent vessel, and biochemical characteristics of the plaque.

To assist a clinician in understanding the risk of plaque rupture and thus identify stable and vulnerable plaque for a given patient, a machine-implemented plaque vulnerability assessment is provided. The machine-based assessment is a second opinion or informs the physician for diagnosis and/or therapy planning. Rather than relying on variability due to different training, skill levels, working environments, or other factors, a machine-implemented classification provides a more objective source of risk information. Since a machine-implementation is used, the plaque assessment in medical imaging may be improved. The machine-implementation may better or more consistently combine different types of information linked to plaque vulnerability.

The assessment is primarily based on medical imaging, augmented by information from computational modeling and/or blood tests. Rather than relying on imaging alone, multiple types of information are gathered for classification. The machine-implementation may more efficiently and rapidly gather and provide the assessment as compared to manual performance.

In one embodiment, medical imaging is performed. Anatomical and morphological features characterizing the plaque and a related vessel or vessels (e.g., parent and/or branching vessel) are extracted from medical images. Hemodynamic computation is performed to extract hemodynamic features characterizing the plaque. Invasive or non-invasive flow and/or pressure measurements are used to find the hemodynamic features. Alternatively or additionally, a computational fluid dynamics (CFD) analysis based on a model personalized from the medical imaging is used.

Biochemical features of the plaque are extracted from the blood-based biomarkers provided by a blood test. The machine-implemented classifier determines a risk-score for plaque rupture based on combining the anatomical, morphological, hemodynamic, and biochemical features. The risk-score indicates a particular plaque of a particular patient as stable or vulnerable.

Figure 1:
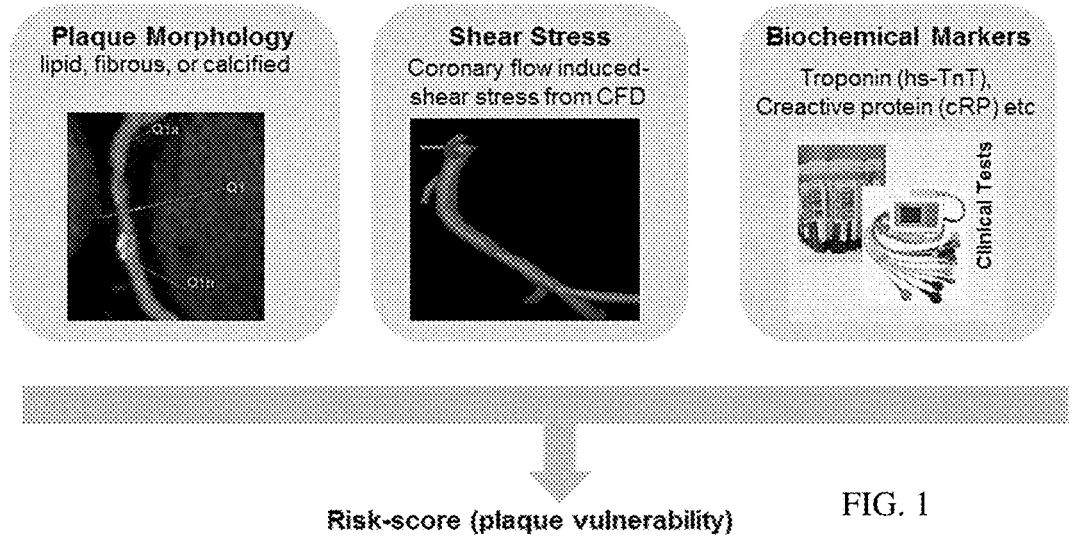
FIG. 1 illustrates one example of combining various plaque assessment-linked features to calculate risk.

FIG. 1 shows an overview of the proposed approach. Analysis of heterogeneous data sources is combined. The morphology of the plaque, such as lipid, fibrous, or calcified, is detected by an image processor from medical imaging data. The hemodynamic stress or other force is calculated as coronary flow induced-shear stress using computational fluid dynamics. for computation fluid dynamics, a model is personalized to the anatomy of the patient, such as using the medical imaging data to personalize the model of the vessel with or without plaque. Biochemical markers, such as Troponin (hs-TnT), creactive protein (cRP), or other feature, are obtained from a clinical test, such as a blood test. Additional, different, or fewer features linked or correlated with risk of plaque rupture or used to determine a further feature linked or correlated with the risk may be used. The risk-score (e.g., plaque vulnerability or other plaque-related risk) is calculated by a machine from the features. The combination of data from many different sources increases the accuracy of the risk calculation, assisting in diagnosis.

Figure 2:
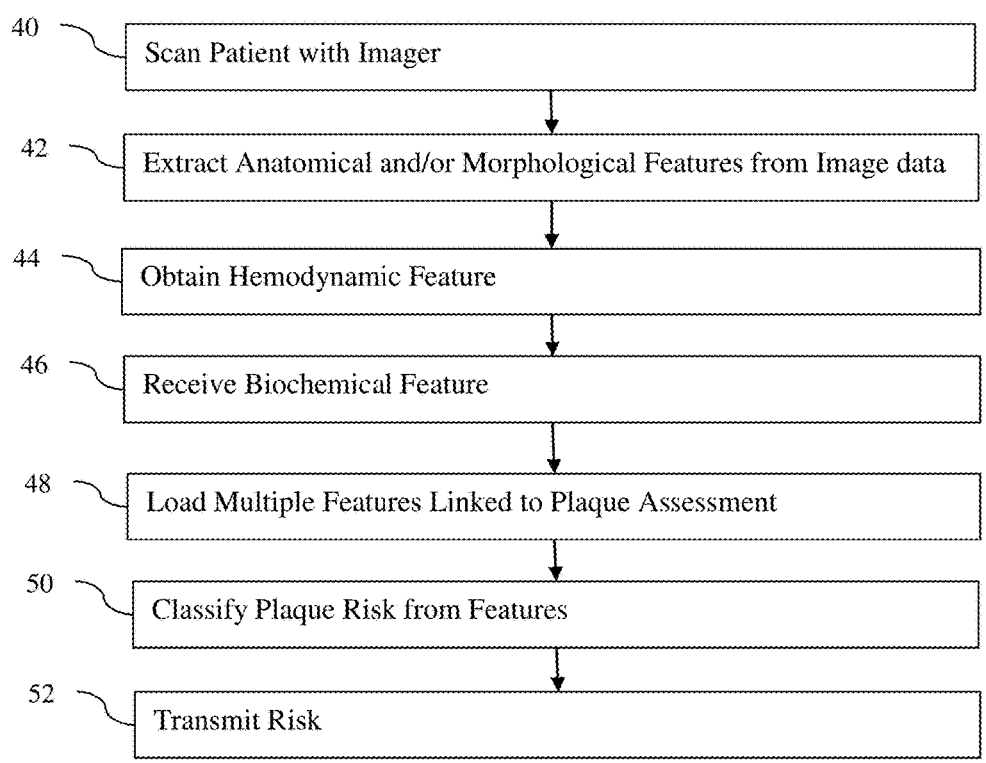
FIG. 2 is a flow chart diagram of one embodiment of a method for assessing plaque vulnerability of a patient in medical imaging.

FIG. 2 is a flow chart diagram of one embodiment of a method for assessing plaque vulnerability of a patient in medical imaging. Information from three or more sources and/or three or more different types of features are loaded and used to classify the risk of plaque rupture or other plaque-related event. The risk is based on different types of information, such as anatomical, morphological, biochemical, and/or hemodynamic, so the resulting risk may be more accurate. Information from any feature linked or correlated with the risk may be combined to determine the risk efficiently and/or consistently with a machine.

Figure 4:
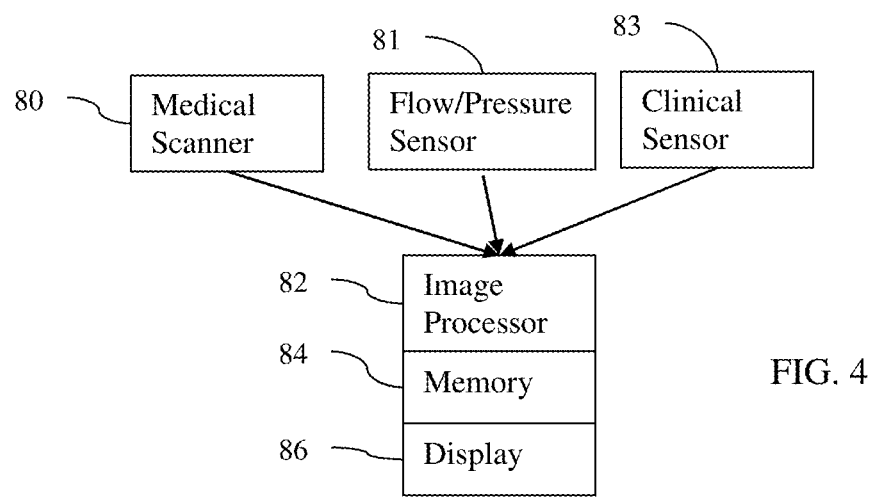
FIG. 4 is one embodiment of a system for assessing plaque vulnerability of a patient in medical imaging.

The method is implemented by the system of FIG. 4 or another system. For example, the method is implemented on an image processor associated with a magnetic resonance (MR), computed tomography (CT), ultrasound, emission, x-ray (e.g., angiography), or other imaging system. As another example, the method is implemented on a picture archiving and communications system (PACS) workstation or server. In other embodiments, the method is implemented in a computer network, such different network nodes or servers performing different acts. The acquisition of the medical data is performed by an imaging system or PACS system. The output is on a display or over the network.

The acts are performed in the order shown (e.g., top to bottom) or other orders. For example, acts 40, 42, 44, and/or 46 are performed in parallel, simultaneously, or in any order.

Additional, different, or fewer acts may be provided. For example, the method is performed without transmitting the risk in act 52. As another example, one of acts 42, 44, and/or 46 are not performed.

In act 40, a medical scanner or imager scans the patient. A medical image or dataset is acquired. The medical image is a frame of data representing the patient. The data may be in any format. While the terms "image" and "imaging" are used, the image or imaging data may be in a format prior to actual display of the image. For example, the medical image may be a plurality of scalar values representing different locations in a Cartesian or polar coordinate format different from a display format. As another example, the medical image may be a plurality red, green, blue (e.g., RGB) values output to a display for generating the image in the display format. The medical image may be currently or previously displayed image in the display or other format. The image or imaging is a dataset that may be used for imaging, such as scan data representing the patient.

Any type of medical image may be used. In one embodiment, the medical image is a computed tomography (CT) image acquired with a CT system. For example, a CT dataset may be used for detecting vessels. As another example, magnetic resonance (MR) data representing a patient is acquired with an MR imager. The MR data is acquired using an imaging sequence for scanning a patient. Data representing an interior region of a patient is acquired. For MR, the magnetic resonance data is k-space data. Fourier analysis is performed to reconstruct the data from the k-space into a three-dimensional object or image space. For CT, the raw data is reconstructed into a three-dimensional representation. Other medical imaging modalities for acquiring the scan data include X-ray angiography (XA), optical coherence tomography (OCT), ultrasound (US), intra-vascular ultrasound (IVUS), and near-infra red spectroscopy (NIRS).

The medical image data or scan data represents tissue of the patient. Alternatively, the medical image represents flow, velocity, or fluids within the patient. In other embodiments, the data represents both flow and structure.

The medical data represents a one, two, or three-dimensional region of the patient. For example, the medical data represents an area or slice of the patient. Values are provided for each of multiple locations distributed in two or three dimensions. The medical data is acquired as a frame of data. The frame of data represents the scan region at a given time or period. The dataset may represent the area or volume over time, such as providing a 4D representation of the patient.

The medical image or dataset is acquired by a scan of the patient. The acquisition occurs as part of the scan. Alternatively, the acquisition is from storage or memory, such as acquiring a previously created dataset from a PACS.

In act 42, an anatomical feature of a vessel or plaque and a morphological feature of the plaque are extracted from the scan of the patient by the medical imaging scanner. The feature extraction is performed by the scanner (e.g., during the time of image reconstruction) or by another device, such as an imaging workstation or the image processor.

Medical image-based features are extracted. Different types of medical imaging data may be used to analyze plaque in blood vessels. The different medical imaging modalities have distinct advantages and disadvantages. Only one modality is used, but multiple modalities are used in other embodiments. Imaging studies indicate plaque information (e.g., calcification status, subtypes, overall burden, attenuation, extent of remodeling, etc.) and eventual correlation with rupture risk. Based on the studies, the modality and/or corresponding features for predicting risk are identified. The identified information is extracted.

One or more morphological features are extracted. The features represent a morphological characteristic of the plaque. For example, the type of plaque is extracted from an angiography scan. Coronary CT angiography may be used to characterize the morphology of the plaque and characterize the morphology into three distinct sub-types—lipid core, fibrous and calcified plaque. Other morphology may include density, elasticity, or other characteristic of the plaque material.

The morphology is extracted from the medical image data. The plaque is identified by segmentation, such as applying a threshold or other image process. For segmentation, each pixel or voxel is identified as either being in the lumen, vessel wall, or the plaque. Alternatively, the locations of plaque are segmented without segmentation of lumen and vessel wall. The medical image data for the plaque locations is used to determine the characteristic. For example, a histogram analysis of the pixel intensity values or attenuation values (e.g., Housenfield unit in CT) is used to determine ranges, which may then be classified as different plaque sub-types.

The anatomical feature of the plaque and/or the vessel is extracted from the medical image data. The image processor or other device extracts the shape, geometry, inlet angle, outlet angle, location of the plaque relative to the vessel, stenosis of the vessel, vessel size, vessel shape, or combinations thereof. Other features correlating with plaque risk or used to calculate a further feature correlating with plaque risk may be extracted. For example, CT angiography is used to quantify the anatomy of the coronary vessel tree, including the stenosis (if present) and the main and side-branches. Other anatomic features of the plaque, such as the shape, geometry, inlet and outlet angles, location (e.g., bifurcation or otherwise) may be extracted from CT angiography images.

The anatomical structure is located by the image processor. The identification is of locations of the structure, such as the vessel. Any now known or later developed approach to locate the anatomical structure may be used. For example, an adaptive region growing and skeletonization approach is used. One or more seeds, such as those in/for the vessel, are located by the processor or manual entry. The seed or seeds are used in region growing to find locations of the vessel tree. Skeletonization may be used to model the vessel structure, such as using lines to represent the centers of the branches of the vessel tree.

Using threshold, random walker, or other approach, the vessel and/or plaque of interest may be segmented for calculating anatomical features. The vessel and/or plaque as detected from the medical image data for a specific patient may be modeled. A generic model of the vessel and/or plaque is fit to the segmented anatomy or to locations identified as vessel. Any fitting may be used. The fit model is then used to calculate the anatomical feature or features, such as a smallest area in a stenosis. Alternatively, the anatomical features are calculated from the segmentation and/or location information without fitting a model.

The morphological and/or anatomical features are extracted automatically with a processor or semi-automatically with the processor and user input. Under a fully-automated approach, an underlying image-processing algorithm detects the anatomical region of interest. For example, the algorithm automatically detects the stenosis and/or plaque by filtering, thresholding, pattern matching, and/or other image process. Then, the anatomical features are extracted by the processor from the medical image data representing the detected regions. This automatic approach occurs without user input of locations of the anatomy.

Under a semi-automated approach, some of the features may be extracted automatically by an algorithm, while some others may be annotated or edited/corrected by a human. Alternatively, the user inputs a seed location using a user input device, and the processor then extracts the feature using the seed location. In another example, the user places calipers or other measuring tools, and the processor determines the value of the feature from the calipers.

In alternative approaches, one or more features are extracted manually. The user views an image and manually determines the value of the feature. The user enters an annotation or fills in a field with the value of the manually determined feature.

In act 44, the image processor obtains one or more hemodynamic features of the patient. The image processor obtains the features from a sensor and/or from personalized modeling of the vessel based on the scan. The value or values of the hemodynamic feature or features are obtained from the image processor modeling, from an output by the sensor, and/or from memory. The hemodynamic sensor may be a flow and/or pressure sensor, such as from a pressure cuff and a Doppler flow sensor or from a pressure and flow sensor wire in a catheter within the patient. For computational flow modeling, a physics-based or computation flow dynamics model is fit to the anatomy of the patient (i.e., personalized) detected from the medical imaging data. A machine-learning based model for predicting the flow, pressure, and/or shear stress may be used in place of the physics-based model. Alternatively, phase-contrast MR imaging or other imaging may be used to measure the value of the feature directly.

The sensor and/or personalized model may be used to extract one or more features for then calculating a feature linked to plaque risk. For example, a pressure, flow, or pressure and flow are extracted. Stress or other force applied to the plaque or vessel by the plaque is calculated from the pressure, flow, or pressure and flow. Any hemodynamic feature may be used.

Shear stress has a mechanistic role in the progression and eventual rupture of coronary plaque. Wall stresses, such as shear stress, normal stress, or total stress, may be assessed by either measuring flow and/or pressure. Other forces may be extracted.

In other embodiments, the modeling to calculate the stress includes both the anatomical model and material properties of the plaque and/or vessel. For example, the plaque detected from the medical images is associated with one or more material properties. The material properties may then be used in conjunction with flow modeling through the anatomy to perform a fluid-structure interaction (FSI) computation of the force or forces acting on the plaque.

In one embodiment, the values for the anatomical, morphological, and/or hemodynamic features are extracted without invasion of the patient. The measurements used to calculate the values rely on sensors exterior to the patient. For example, the medical imaging scanner is a CT, MR, or ultrasound sensor (e.g., detector, source, transducer, and/or antennas) located outside of the patient. Modeling based on medical imaging derived anatomy or other measures from outside the patient are used for extracting the values of the features.

In alternative embodiments, one or more invasive procedures or devices are used, such as an intravascular ultrasound catheter or pressure/flow sensor from within the patient. Features from invasive modalities, such as IVUS, OCR or NIRS, correlate to plaque risk. For non-invasive, the same data correlated with risk may be derived from non-invasive imaging, such as CTA imaging. The same hypothesis for the link or correlation to plaque risk may be used, but based on a measure from non-invasive imaging. For example, CTA imaging is used to extract a morphological feature as used in a hypothesis proposed for IVUS.

In act 46, an interface receives the values for one or more biochemical features. The interface is a user input, port, memory connector, or other device for receiving data. The biochemical feature value is from a blood test of the patient. The results of the blood test are transmitted to, retrieved from memory through, loaded through, or input to the interface.

Any biochemical feature may be used. For example, a level of serum C-reactive protein (CRP), high sensitive troponin T, or both are received. Any now known or later developed blood biomarker linked or correlated with plaque risk may be used. The level of serum CRP is a prognostic factor for acute coronary events and sudden cardiac death, and is associated with coronary calcification. CRP and coronary plaque subtypes may be correlated. Advanced plaque analysis from coronary CTA and high sensitive troponin T (hsTnT) may correlate with risk and be used for risk stratification.

In act 48, the image processor loads the morphological characteristic of plaque of the patient, hemodynamic characteristic, anatomy characteristic of the vessel with the plaque, and biochemical characteristic of the plaque as an input feature vector. The values for the various types of features are accessed from memory, any interface, and/or received in response to a query by or push to the image processor. These values of the various types of features are loaded as an input vector for classification. Other types of values may be loaded as well. The values are loaded into memory, the image processor, or a database for access by the image processor.

In act 50, the image processor or other device classifies the plaque of the patient. A machine-implemented classifier calculates a risk of rupture or other plaque-related prediction from the input vector. The classifier determines a risk score for the patient based on the information or input feature vector related to plaque. The determination of risk score is achieved by combining the anatomical, morphological, hemodynamic, and/or biochemical features.

In one embodiment, the machine-implemented classifier calculates the risk as a weighted sum. Some or all of the features of the input vector individually or independently correlate with the risk. Based on studies or other knowledge, this relation to risk is used for each feature. The weighting may account for the different dynamic ranges of the values for the different features and/or the strength of correlation of the feature to the risk. The results from the different correlated features are combined. The machine-implemented classifier calculates the risk as a weighted sum of ranks mapped from each of the anatomical, morphological, hemodynamic, and biochemical features. Each individual score from a given feature is computed by using the already established hypothesis for these respective factors from the clinical literature. These scores are weighted, and the weighted scores are summed, computing a composite risk score.

Other machine-implemented classifiers may be used. For example, a mechanistic model is used. The mechanistic model uses the input features to personalize the model to the patient. The personalized model is then used to calculate the risk.

Other machine-implemented classifiers may be used, such as data-driven models. In one embodiment, the machine-implemented classifier is a machine-learnt classifier. A matrix relating (e.g., with weights) the values of the input vector (e.g., features) to output risk scores is learnt from training data with known risk. The image processor or other machine applies the matrix as the machine-implemented classifier. The machine-learnt or machine-trained classifier combines the various features into a risk score. Different values of the features result in different predicted risks.

Machine-learnt classifiers involve two phases, a training phase and a prediction phase. During the training phase, the machine-learning algorithm is 'trained' on a database containing multiple training examples together with ground truths. The training database may be populated in any manner. For example, positive training examples are the plaques that ruptured, and negative examples (e.g., from the same patient) are the plaques that did not rupture during an acute coronary syndrome event. The training examples from many different patients are gathered. In another example, the training examples are gathered from patients before and after rupture and other patients over the same period but without rupture. In yet another example, the "ground truth" for the training data may be prepared by considering inputs from one or several clinicians rather than by actual event or rupture. The classifier learns how the clinicians prescribe rupture risk to plaque. In another example, a product of experts (PoE)-based machine learning algorithm or a deep-learning algorithm can be used to achieve this.

Any machine learning or training may be used. In one embodiment, a neural network is used. Other deep learnt, sparse auto-encoding classifiers may be trained and applied. In alternative embodiments, a Bayes network or support vector machine is trained and applied. Hierarchal or other approaches may be used. Supervised or semi-supervised machine learning may be used. Any machine learning method may be used.

The image processor or other machine applies the machine-learnt classifier by input of values of the features. The output is risk. The risk may be binary, such as indicating plaque as vulnerable or stable. In other embodiments, a probability or confidence in the classification is returned, such as predicting the risk of rupture with any resolution. The classifier outputs an indication of the likelihood that the plaque will rupture or other plaque-related risk.

The machine-implemented classifier may be used for any of various purposes and/or patient analyses. The risk of rupture is predicted in one embodiment. In another embodiment, risk stratification is provided. For example, both risk stratification and plaque vulnerability assessment are calculated from or as the risk score for the patient in a coronary artery disease analysis. Combined analysis of cardiac biomarkers (e.g., C-reactive protein, Troponin—hsTnT), imaging biomarkers (e.g., plaque and stenosis analysis from CTA), and physiological modeling (e.g., blood flow, shear stress, computed fractional flow reserve) is used for risk stratification and plaque vulnerability index for stable coronary artery disease patients. In another example, the risk score is calculated for the patient in an acute coronary syndrome analysis. Combined analysis of cardiac biomarkers (e.g., C-reactive protein, Troponin—hsTnT), imaging biomarkers (e.g., plaque and stenosis analysis from non-invasive CTA, and/or invasive angiography, IVUS, OCT), and physiological modeling (e.g., blood flow, shear stress, computed fractional flow reserve) is used for acute coronary syndrome patients.

In act 52, the image processor or other device transmits the risk score for the patient. The transmission is to a memory, a network, a display, a printer, or other device. The transmission is wired and/or wirelessly.

The transmission signals a result of the classification to one or more users. Transmission of a risk score to a display, medical record, printer, or other output assists the user in diagnosis or therapy planning.

Figure 3:
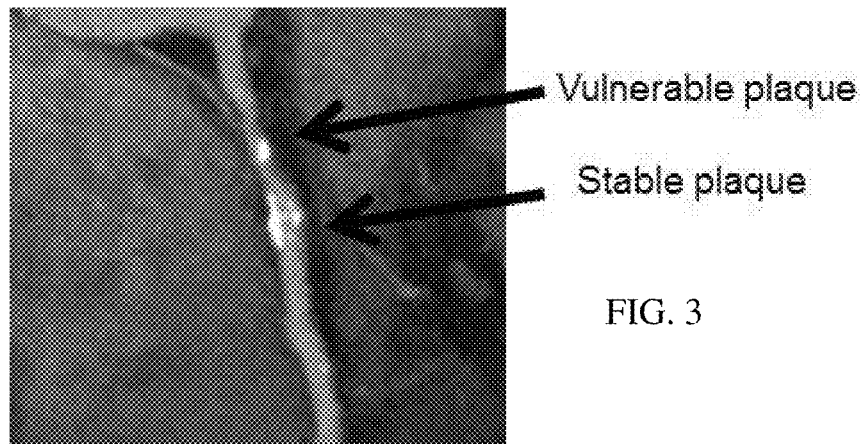
FIG. 3 illustrates an example image showing relative risk between two locations of plaque in a vessel.

The risk score is presented as alphanumeric text. Alternatively, the risk score is presented in an image, such as using color coding, annotation, and/or other indicators of risk on a one-dimensional vessel skeleton or flattened vessel, a two-dimensional image, or a three-dimensional rendering. For example, FIG. 3 shows a CTA image of a cross-section along a vessel with two regions of plaque shown as brighter than the vessel or surrounding tissue. Annotations indicate the classified risk score for each plaque. Color or other indicators may be used, such as coloring the vulnerable plaque with a shade of red and the stable plaque with a shade of blue. The risk is indicated on any image of the vessel.

A given patient and/or vessel of a patient may have different regions of plaque. Each plaque is assessed for risk. The extraction of anatomical and/or morphological features is repeated for each plaque. The hemodynamic features are obtained for each plaque. Where the same stress is applied to each plaque do to being in the same vessel branch, the obtaining of the hemodynamic features may not be repeated. Since the vessel has different shapes and/or sizes at different locations, the obtaining of the hemodynamic features may be repeated but using a model common to multiple plaques. The receipt of the biochemical features is not repeated as the blood test results are applicable to any plaque in a given patient. If the biochemical features are received from more direct sampling of a plaque, then the receipt may be repeated for different plaques. The loading and classification are repeated to classify the risk for each plaque. The classification is applied separately to each such plaque, generating individual or plaque specific risk-scores. Additionally or alternatively, a combined score may be formulated by combining information from multiple plaques. The combination is an average or selection of the greatest risk. The combination represents the risk of plaque rupture occurring for a patient rather than the risk for a specific plaque.

FIG. 4 shows a system for assessing plaque vulnerability of a patient in medical imaging. The system includes a medical scanner 80, a flow/pressure sensor 81, a clinical sensor 83, a memory 84, an image processor 82, and a display 86. Additional, different, or fewer components may be provided. For example, the memory 84, an interface, and/or a patient medical record database are provided for the hemodynamic and/or biochemical features instead of the flow/pressure sensor 81 and/or clinical sensor 83. As another example, an interface is provided for receiving features. In yet another example, a network or network connection is provided, such as for networking with a medical imaging network or data archival system without using the medical scanner 80. In another example, a user interface is provided for manual entry of features.

The image processor 82, memory 84, and display 86 are part of the medical scanner 80. Alternatively, the image processor 82, memory 84, and display 86 are part of an archival and/or image processing system, such as associated with a medical records database workstation or server, separate from the medical scanner 80. In other embodiments, the image processor 82, memory 84, and display 86 are a personal computer, such as desktop or laptop, a workstation, a server, a network, or combinations thereof. The image processor 82, display 86, and memory 84 may be provided without other components for acquiring data by scanning a patient.

The medical scanner 80 is a medical diagnostic imaging system. Ultrasound, IVUS, CT, CTA, OCT, x-ray, angiography, fluoroscopy, positron emission tomography, single photon emission computed tomography, NIRS, and/or MR systems may be used. The medical scanner 80 may include a transmitter and includes a detector for scanning or receiving data representative of the interior of the patient. The medical scanner 80 scans the vessel and/or plaque in the patient.

In one embodiment, the medical scanner 80 is a CT system. An x-ray source is connected with a gantry. A detector is also connected with a gantry opposite the x-ray source. The patient is positioned between the source and detector. The source and detector are on opposite sides of the patient and rotate and/or translate about the patient. The detected x-ray energy passing through the patient is converted, reconstructed, or transformed into data representing different spatial locations within the patient. For CTA, a radiopaque contrast agent is provided in the blood of the patient. Other angiography systems may be used, such as an x-ray or dedicated angiography system. The angiography system includes an x-ray source and detector.

As an ultrasound or IVUS, a transducer is positioned so that the vessel is scanned with acoustic energy. An array of elements in the transducer is used to steer the acoustic energy. The received acoustic echoes are converted to electrical energy, beamformed, and detected, such as with Doppler and/or B-mode detection.

In another embodiment, the medical scanner 80 is a MR system. The MR system includes a main field magnet, such as a cryomagnet, and gradient coils. A whole body coil is provided for transmitting and/or receiving. Local coils may be used, such as for receiving electromagnetic energy emitted by atoms in response to pulses. Other processing components may be provided, such as for planning and generating transmit pulses for the coils based on the sequence and for receiving and processing the received k-space data. The received k-space data is converted into object or image space data with Fourier processing.

The flow and/or pressure sensor 81 is an invasive or non-invasive sensor. For example, a cuff is used to measure pressure. A Doppler sensor, such as a dedicated flow sensor or by use of an ultrasound scanner, measures flow. In another example, a flow and/or pressure sensor on a catheter measures the flow and/or pressure within the patient.

The clinical sensor 83 is any clinical testing device. For example, a spectrometer, microscopic examination, chemical reaction, or other testing device is used. To obtain the blood for the clinical sensor 83, blood is drawn from an arm of the patient. Alternatively, the blood is withdrawn from a location near the plaque, such as using a catheter.

The memory 84 may be a graphics processing memory, a video random access memory, a random access memory, system memory, cache memory, hard drive, optical media, magnetic media, flash drive, buffer, database, combinations thereof, or other now known or later developed memory device for storing data or video information. The memory 84 is part of the medical scanner 80, part of a computer associated with the image processor 82, part of a database, part of another system, a picture archival memory, or a standalone device.

The memory 84 stores medical imaging data representing the patient, segmentation information, acquired values for features, a model, parameters of a personalized model, classification results, a machine-learnt matrix, and/or images. Any features received from other sources, such as the medical scanner 80, the flow/pressure sensor 81, or clinical sensor 83, are stored. Data from the scanner 80 or sensors 81, 83 used to derive features may be stored. Values for features received at an interface or calculated by the image processor 82 are stored. For example, biochemical features from a blood test entered on a user input, received from a laboratory, or provided by another source are stored in the memory 84. The memory 84 may alternatively or additionally store data during processing.

The memory 84 or other memory is alternatively or additionally a non-transitory computer readable storage medium storing data representing instructions executable by the programmed image processor 82. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 82 is a central processing unit, control processor, graphics processor, digital signal processor, three-dimensional rendering processor, application specific integrated circuit, field programmable gate array, digital circuit, analog circuit, combinations thereof, or other now known or later developed device for assessing plaque risk. The image processor 82 is a single device or multiple devices operating in serial, parallel, or separately. The image processor 82 may be a main processor of a computer, such as a laptop or desktop computer, or may be a processor for handling some tasks in a larger system, such as in an imaging system. The image processor 82 is configured by instructions, design, hardware, and/or software to perform the acts discussed herein.

The image processor 82 is configured to extract one or more features of the vessel, plaque, or vessel and plaque from data of the scan by the medical scanner 80. Any anatomical, morphological, or anatomical and morphological features of the vessel, plaque, or vessel and plaque are extracted. Segmentation, pattern matching, classification, or other image process is used to determine values for features of the vessel and/or plaque.

In one embodiment, the image processor 82 is configured to calculate stress and/or other force to which the plaque is subjected or in the vessel. Measurements of flow and/or pressure may be used. Alternatively, the image processor 82 implements modeling to calculate the stress or other force. For example, a generic vessel and/or plaque model is fit to scan data from the patient. Measurements of pressure and/or flow may be used, in addition to scan data, to fit the model. The personalized model is used to calculate the flow or pressure, from which the stress is calculated. The personalized model may be used to directly calculate the stress rather than using an intermediary calculation of the flow and/or pressure. In one approach, a hemodynamic feature or features are calculated using a fluid-structure interaction computation derived from the scan by the medical scanner 80.

The image processor 82 is configured to determine a risk of rupture of the plaque from the features. A combination of two or more of anatomical, morphological, biochemical, and/or hemodynamic features is used to determine the risk. Any number of features of a given type may be used. A classifier implemented by the image processor 82 determines the risk. The classifier may use a weighted sum or mechanistic model. In one embodiment, the classifier is a machine-learnt classifier with the features as part of an input vector of the machine-learnt classifier. The values of the features are input to the classifier. The image processor 82 outputs the risk based on the input vector.

The display 86 is an output. Other outputs may be used, such as an interface, network connector, or printer. The output is configured to output the risk of rupture or other risk related to plaque for the patient.

The display 86 is monitor, LCD, projector, plasma display, CRT, printer, or other now known or later developed device for outputting visual information. The display 86 receives images, graphics, text, quantities, or other information from the image processor 82, memory 84, or medical scanner 80. One or more medical images are displayed. The images are of a region of the patient. In one embodiment, the images are of a vessel or vessel tree. The locations of the plaque located by the image processor 82 are highlighted or displayed with other tissue or fluid without highlighting. The image includes an indication, such as a graphic or colorization, of the risk for each plaque or plaque in general for the patient. Alternatively or additionally, the image includes a quantity based on the classification, such as the risk score value. The quantity may be displayed as the image without the medical image representation of the patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for assessing plaque vulnerability of a patient in medical imaging, the method comprising:
    extracting an anatomical feature of a vessel or plaque and a morphological feature of the plaque from a scan of the patient by a medical imaging scanner;
    obtaining a hemodynamic feature of the patient from a hemodynamic sensor or personalized modeling of the vessel based on the scan;
    receiving at an interface a biochemical feature from a blood test of the patient, the biochemical feature including a level of high sensitive troponin;
    calculating by a machine-implemented classifier a risk score for plaque rupture for the patient and a risk stratification, both the risk score and risk stratification calculated by the machine-implemented classifier from the anatomical, morphological, hemodynamic, and biochemical features; and
    transmitting the risk score for the patient to a display.

2. The method of claim 1 wherein extracting the morphological feature comprises extracting a type of the plaque from an angiography as the scan.

3. The method of claim 1 wherein extracting the anatomical feature comprises extracting a shape, geometry, inlet angle, outlet angle, location of the plaque relative to the vessel, stenosis of the vessel, vessel size, vessel shape, or combinations thereof.

4. The method of claim 1 wherein extracting comprises extracting automatically with a processor or semi-automatically with the processor and a user input.

5. The method of claim 1 wherein obtaining comprises obtaining a pressure, flow, or pressure and flow and calculating stress from the pressure, flow, or pressure and flow.

6. The method of claim 1 wherein the level of high sensitive troponin is a level of high sensitive troponin T.

7. The method of claim 1 wherein calculating comprises calculating by the machine-implemented classifier as a weighted sum of ranks mapped from each of the anatomical, morphological, hemodynamic, and biochemical features, the weights based on clinical literature.

8. The method of claim 1 wherein calculating comprises calculating by the machine-implemented classifier comprises a mechanistic model.

9. The method of claim 1 wherein calculating comprises calculating by the machine-implemented classifier comprising a machine-learnt classifier.

10. The method of claim 1 wherein calculating comprises calculating the risk score as part of the risk stratification and a plaque vulnerability assessment for the patient in a coronary artery disease analysis.

11. The method of claim 1 wherein calculating comprises calculating the risk score for the patient in an acute coronary syndrome analysis.

12. The method of claim 1 further comprising repeating extracting, obtaining, and calculating for another plaque.

13. The method of claim 1 further comprising performing the scan with the medical imaging scanner comprising a non-invasive modality, wherein the anatomical, morphological, and hemodynamic features are all obtained without invasion of the patient.

14. A method for assessing plaque vulnerability of a patient in medical imaging, the method comprising:
   loading a morphological characteristic of plaque of a patient, a hemodynamic characteristic, an anatomy characteristic of a vessel with the plaque, and a biochemical characteristic of the plaque as an input feature vector, where a biochemical characteristic is a level of high sensitive troponin;
   classifying a vulnerability of the plaque of the patient by a machine-trained classifier in response to the input feature vector, the classifying being part of a risk stratification based on the hemodynamic, biochemical, and anatomy characteristics; and
   signaling a result of the classifying to a user.

15. A method for assessing plaque vulnerability of a patient in medical imaging, the method comprising:
   extracting an anatomical feature of a vessel or plaque and a morphological feature of the plaque from a scan of the patient by a medical imaging scanner;
   obtaining a hemodynamic feature of the patient from a hemodynamic sensor or personalized modeling of the vessel based on the scan;
   receiving at an interface a biochemical feature from a blood test of the patient, the receiving comprising receiving a level of high sensitive troponin;
   calculating by a machine-implemented classifier a risk score for plaque rupture for the patient and a risk stratification, both the risk score and risk stratification calculated by the machine-implemented classifier from the anatomical, morphological, hemodynamic, and biochemical features; and
   transmitting the risk score for the patient to a display.

* * * * *